US012582600B2

(12) United States Patent
Fang et al.

(10) Patent No.: US 12,582,600 B2
(45) Date of Patent: Mar. 24, 2026

(54) STABLE GEL COMPOSITION HAVING HIGH OIL CONTENT, AND PREPARATION METHOD THEREFOR AND APPLICATION THEREOF

(71) Applicant: SIRIO PHARMA CO., LTD., Shantou (CN)

(72) Inventors: Suqiong Fang, Shantou (CN); Yirui Zheng, Shantou (CN); Wenrong Chen, Shantou (CN)

(73) Assignee: SIRIO PHARMA CO., LTD., Shantou (CN)

( * ) Notice: Subject to any disclaimer, the term of this patent is extended or adjusted under 35 U.S.C. 154(b) by 1101 days.

(21) Appl. No.: 17/614,629

(22) PCT Filed: Aug. 27, 2020

(86) PCT No.: PCT/CN2020/111647
§ 371 (c)(1),
(2) Date: Nov. 29, 2021

(87) PCT Pub. No.: WO2021/037122
PCT Pub. Date: Mar. 4, 2021

(65) Prior Publication Data
US 2022/0218603 A1 Jul. 14, 2022

(30) Foreign Application Priority Data

Aug. 29, 2019 (CN) .......................... 201910806809.6

(51) Int. Cl.
| | |
|---|---|
| *A61K 9/00* | (2006.01) |
| *A23L 33/12* | (2016.01) |
| *A23L 33/125* | (2016.01) |
| *A23P 10/30* | (2016.01) |
| *A61K 47/22* | (2006.01) |
| *A61K 47/36* | (2006.01) |
| *A61K 47/44* | (2017.01) |
| *A61K 47/46* | (2006.01) |
| *B65D 65/38* | (2006.01) |

(52) U.S. Cl.
CPC ............ *A61K 9/0056* (2013.01); *A23L 33/12* (2016.08); *A23L 33/125* (2016.08); *A23P 10/30* (2016.08); *A61K 47/22* (2013.01); *A61K 47/36* (2013.01); *A61K 47/44* (2013.01); *A61K 47/46* (2013.01); *B65D 65/38* (2013.01); *A23V 2002/00* (2013.01)

(58) Field of Classification Search
CPC ....................................................... A61K 9/00
USPC ........................................................ 424/440
See application file for complete search history.

(56) References Cited

U.S. PATENT DOCUMENTS

| | | | |
|---|---|---|---|
| 7,531,192 B2 | 5/2009 | Farber et al. | |
| 2015/0099053 A1 | 4/2015 | Kugitani et al. | |

FOREIGN PATENT DOCUMENTS

| | | | | | |
|---|---|---|---|---|---|
| CN | 101389310 | * | 6/2014 | ............... | A61K 9/00 |
| CN | 101389310 | B | 6/2014 | | |
| CN | 109287770 | A | 2/2019 | | |
| CN | 109414052 | A | 3/2019 | | |
| CN | 110478312 | A | 11/2019 | | |
| EP | 1046347 | A1 | 10/2000 | | |
| ES | 2340482 | T3 | 6/2010 | | |
| JP | 63157934 | A | 6/1988 | | |
| JP | 2004298061 | A | 10/2004 | | |
| JP | 2019088238 | A | 6/2019 | | |
| WO | 2010041015 | A2 | 4/2010 | | |
| WO | 2012046066 | A1 | 4/2012 | | |
| WO | WO-2016066256 | A1 * | 5/2016 | ............. | A61K 47/14 |
| WO | 2018008715 | A1 | 8/2018 | | |

OTHER PUBLICATIONS

IOI Oleochemical Pharma brochure "Softigen Compendial liquid solubilizer" www.ioioleo.de/wp-content/uploads/2022/09/IOI_Pharma_Excipients_2022 (Year: 2022).*
European Search Report for EP Application No. 20858155.3 dated Apr. 18, 2023, 6 pages.
Office Action for Japanese Patent Application No. 2022-513135 dated Apr. 18, 2023 with English translation, 8 pages.
International Search Report of International Application No. PCT/CN2020/111647 mailed Dec. 3, 2020, 4 pgs.
Zhong, Jinfeng, "Advances in Oleogels and Their Applications in Food Industry", Food Science, Feb. 15, 2015, vol. 36, No. 3, English Abstract.
Cao et al., "Advance in Technology of Edible Vegetable Oil-Gelling", China Oils and Fats, Aug. 20, 2019, vol. 44, No. 8, English Abstract.

* cited by examiner

*Primary Examiner* — Walter E Webb

(74) *Attorney, Agent, or Firm* — Lowenstein Sandler LLP

(57) ABSTRACT

A chewable stable gel composition having a high oil content, comprising, on the basis of the total weight of the composition, 55-70 wt % oil, 1-15 wt % first gelling agent, 0.1-2 wt % second gelling agent, 0.1-7 wt % stabilizer, optional other additives for medicine, food, and/or a health care product, and the balance of water. Also provided are a preparation method for and an application of the gel composition.

13 Claims, 2 Drawing Sheets

Test sample: fish oil (without hydrogenated palm oil), the coefficient of viscosity is 0.85.

Test sample: fish oil + hydrogenated palm oil, the coefficient of viscosity is 1.03.

STABLE GEL COMPOSITION HAVING HIGH OIL CONTENT, AND PREPARATION METHOD THEREFOR AND APPLICATION THEREOF

CROSS-REFERENCE TO RELATED APPLICATIONS

This application is a U.S. national stage filing, under 35 U.S.C. § 371 (c), of International Application No. PCT/CN2020/111647, filed on Aug. 27, 2020, which claims priority to Chinese Patent Application No. CN201910806809.6, filed on Aug. 29, 2019. The entire contents of each of the aforementioned applications are incorporated herein by reference.

TECHNICAL FIELD

The present application generally relates to a gel composition, and more specifically, to a stable gel composition with a high oil content. The application also relates to preparation method and use of the gel composition.

BACKGROUND OF THE INVENTION

Unsaturated fatty acid esters, especially polyunsaturated fatty acid esters, are important sources of essential fatty acids. Unsaturated fatty acid esters (such as fish oil, etc.) are widely used as nutritional supplements at present. However, the taste and mouthfeel of unsaturated fatty acid esters such as fish oil are often unbearable. Thus, unsaturated fatty acid esters usually are delivered as forms such as soft capsules. The shell of such capsules is often made of gelatin from a mammalian (for example, derived from pigs or cattles). However, in the prior art, in order to deliver an appropriate dose of oil, the capsules of the gel composition generally tend to be prepared in a larger volume, and such a preparation process will cause a problem that the capsules are difficult to be swallowed by young children and the elderly. In addition, the ingestion process of such capsules is often accompanied by the problem of the capsule shell rupturing in the mouth, so that the unpleasant taste of the capsule oil content is released in the oral cavity, leaving a negative impression on the consumers, thereby reducing the initiative to ingest the capsule.

In recent years, an oil-in-water chewable gel composition has been used in the fields of food, medicine and health care products. The aqueous phase of the composition is gelled and the oil phase contains unsaturated fatty acid esters or other oil-soluble active substances. Such gel composition is usually called "oil gel", "gel oil", "structured oil" or "lipid gel", etc. The products on the market are mostly called "fish oil jelly" or "jelly fish oil". For example, CN101389310B discloses a chewable emulsion comprising physiologically tolerable unsaturated fatty acid esters, which contains 30 to 50 wt % of the oil phase ingredients.

However, the existing "oil gel" or "fish oil jelly" often has the problem of a relatively low oil content (for example, less than 50 wt %), which makes the delivery efficiency of an active substance not high. In addition, since a composition with a high oil content (for example, an oil content higher than 50 wt %) is prone to oil-water separation, there is a problem of oil precipitation on the surface of the product during storage. This results in a low storage stability of oil gel products and also causes problems such as a loose texture and a poor chewing feeling.

Therefore, how to increase the oil content in a composition and prepare a stable gel composition has become a common problem in this field.

SUMMARY OF THE INVENTION

The inventors have unexpectedly found that a significantly increased oil content (for example, to more than 50 wt %) and stability of an oil gel product can be achieved by using a combination of two gelling agents and stabilizers at a specific ratio, and the oil precipitation on the surface caused by the oil-water separation along with the flavor of the products can be improved, and the greasy taste during consumption can be reduced. Also, the texture (such as hardness, elasticity, cohesiveness) of the products is improved, so as to obtain a composition with a higher delivery efficiency, an improved stability, and a better mouthfeel.

In order to solve the above problems, the technical solution in this application is as follows: a gel composition, characterized in that, based on the total weight of the gel composition, the gel composition comprises: (1) 1 to 15 wt % of a first gelling agent, wherein the first gelling agent is selected from a group consisting of gelatin, carrageenan, pectin, konjac gum, and guar gum; (2) 0.1 to 7 wt % of a stabilizer, which is a mixture of 2 to 5 wt % of a hydrogenated palm oil, a palm stearin or a beeswax and 0.2 to 1 wt % of a phospholipid; and (3) 55 to 70 wt % of an oil other than the hydrogenated palm oil and/or the palm stearin. Preferably, the gel composition is in a chewable and edible oil-in-water type.

In one embodiment, the gel composition further includes a second gelling agent, wherein the second gelling agent is selected from a group consisting of xanthan gum, agar, gellan gum, locust bean gum, arabic gum, and modified starch.

In one embodiment, the first gelling agent is gelatin, and the second gelling agent is xanthan gum.

In one embodiment, the melting point of the hydrogenated palm oil or palm stearin ranges from 39° C. to 65° C.

In one embodiment, the oil is an unsaturated fatty acid or its esters.

In one embodiment, the oil is an animal oil, a vegetable oil, or a combination thereof.

In one embodiment, the oil is a fish oil, an algae oil or a combination thereof.

In one embodiment, the gel composition further comprises an additive useful in medicines, foods, or health care products, wherein the additive is one or more of a sweetener, an acid regulator, a filler, a flavoring agent, a coloring agent, and an antioxidant.

In one embodiment, the sweetener is xylitol, and/or sorbitol; the acid regulator is citric acid and its salts, and/or malic acid; the filler is resistant dextrin, and/or inulin; the flavoring agent is an oil-soluble essence, and/or a water-soluble essence; the coloring agent is an oil-soluble pigment and/or a water-soluble pigment; the antioxidant is vitamin E, rosemary extract, and/or polyphenols.

In one embodiment, the aqueous phase of the gel composition further comprises a water-soluble active ingredient, wherein the active ingredient is selected from a group consisting of a water-soluble vitamin, a water-soluble dietary fiber and a mineral; and the oil phase of the gel composition further includes an oil-soluble vitamin.

In another aspect, the present invention also provides a method for preparing the above gel composition, comprising:

(1) heating the first gelling agent in water at a temperature between 60 and 80° C. until the first gelling agent completely dissolves;

(2) adding the stabilizer to the oil and mixing them homogeneously;

(3) mixing the mixture obtained in the step (1) and the mixture obtained in the step (2) at a temperature between 60° C. and 80° C. homogeneously, and subjecting to homogenization and emulsification for 3 to 8 minutes; and (4) shaping the mixture obtained in the step (3) to obtain the desired gel composition, wherein the shaping is achieved by one of the following methods:

(a) pouring the mixture obtained in the step (3) to a blister;

(b) filling the mixture obtained in the step (3) into a capsule; and (c) packaging the mixture obtained in the step (3) in a packaging material, wherein the packaging material comprises one or more of an aluminum-plastic composite pouch and a packaging container made of a thermoresistant material.

In one embodiment, the method comprises the following steps after the homogenization and emulsification in the step (3): adding a second gelling agent; then subjecting to homogenization and emulsification for 7 to 15 minutes; wherein the second gelling agent is one or more of xanthan gum, agar, gellan gum, locust bean gum, acacia gum, and modified starch.

In another aspect, the present invention also provides an edible composition, which comprises the above-mentioned gel composition.

In one embodiment, the edible composition is a food, medicine or health care product.

In order to solve the above problems, the present application also provides a stable chewable gel composition with a high oil content, wherein an aqueous phase is gelled and may contain an active substance, and wherein an oil phase contains a biologically active ingredient such as an unsaturated fatty acid or its ester and/or an oil-soluble active ingredient. In one aspect, the active substance in the aqueous phase is a water-soluble active ingredient, and more preferably, the active ingredient is selected from a group consisting of a water-soluble vitamin, a water-soluble dietary fiber, a mineral or mixtures thereof. In another aspect, the oil-soluble active ingredient in the oil phase is selected from a group consisting of oil-soluble vitamins.

In one embodiment of the present application, a gel composition is provided. Based on the total weight of the gel composition, the gel composition contains: (1) 55 to 70 wt % of an oil; (2) 1 to 15 wt % of a first gelling agent; (3) 0.1 to 2 wt % of a second gelling agent; and (4) 0.1 to 7 wt % of a stabilizer; (5) optionally, other additives useful in a medicinal, food and/or health care product; and (6) wherein the balance is water.

In one aspect, the first gelling agent is selected from a group consisting of gelatin, carrageenan, pectin, konjac gum, guar gum and other gelling agents and the combination thereof. Preferably, the first gelling agent is gelatin, gelatin and pectin, carrageenan and konjac gum, or carrageenan. Preferably, the mass ratio of gelatin to pectin ranges from 2:1 to 12:1. Preferably, the mass ratio of konjac gum to carrageenan ranges from 1:4 to 3:1.

In another aspect, the second gelling agent is selected from a group consisting of xanthan gum, agar, gellan gum, locust bean gum, acacia gum, modified starch and other gelling agents and any combination thereof. Preferably, the second gelling agent is xanthan gum, arabic gum, arabic gum and modified starch, locust bean gum, or gellan gum. Preferably, the mass ratio of arabic gum to modified starch ranges from 3:1 to 5:1.

In yet another aspect, the stabilizer is selected from a group consisting of palm oil (which is formed by a processing method selected from a group consisting of hydrogenation, refining, transesterification, and fractionation and is a palm oil product having a melting point of 39 to 65° C.), phospholipid, phytosterol, edible waxes and other substances with similar effects and any combination thereof. Preferably, the stabilizer is selected from a group consisting of hydrogenated palm oil, palm stearin, beeswax, phospholipid and a mixture thereof. In one aspect, the stabilizer is a mixture of hydrogenated palm oil, palm stearin or beeswax and phospholipid, for example, a mixture of hydrogenated palm oil and phospholipid. For example, the stabilizer is a mixture of hydrogenated palm oil and phospholipid at a mass ratio of 3 to 15:1. Preferably, based on the total weight of the gel composition, the phospholipid ranges from 0.2 to 1 wt %.

In still another aspect, the oil is selected from a group consisting of an oil containing an unsaturated fatty acid or esters thereof. Preferably, the oil is selected from a group consisting of an animal oil, a vegetable oil and combinations thereof. More preferably, the oil is selected from a group consisting of a fish oil, an algae oil, and combinations thereof. In a further aspect, the oil may also optionally contain one or more other additives useful in a medicine, food, and health care product. Preferably, the biologically active is the oil-soluble vitamin E etc.

In still another aspect, the one or more other additives comprise one or more components selected from a group consisting of a sweetener selected from a group consisting of xylitol, sorbitol and other alditols; an acid regulator selected from a group consisting of citric acid and its salts, malic acid and other acid regulators; a filler selected from a group consisting of resistant dextrin, inulin and other fillers; a flavoring agent selected from a group consisting of an oil-soluble essence, a water-soluble essence and other food essences; a coloring agent selected from a group consisting of a food grade pigment or a coloring fruit and vegetable juice such as an oil-soluble pigment and a water-soluble pigment; and an antioxidant selected from a group consisting of vitamin E, rosemary extract, polyphenol and other antioxidants.

In still another aspect, the gel composition is an oil-in-water gel emulsion, wherein the aqueous phase is gelled and contains an active ingredient and wherein the oil phase contains an unsaturated fatty acid or esters thereof and/or an oil-soluble active ingredient. Preferably, the active ingredient in the aqueous phase is a water-soluble active ingredient, for example selected from a water-soluble vitamin, a water-soluble dietary fiber, a mineral or a combination thereof. Preferably, the oil-soluble active ingredient in the oil phase is selected from an oil-soluble vitamin.

In still yet another aspect, the gel composition is in an oral form, such as a chewable form.

In another embodiment of the present application, a method for preparing the gel composition as described above is also provided.

In one aspect, the method includes: (1) heating the first gelling agent in water at a temperature between 60 and 80° C. until the first gelling agent completely dissolves; (2) adding the stabilizer to the oil and mixing them homogeneously; (3) mixing the mixture obtained in the step (1) and the mixture obtained in the step (2) at a temperature between 60° C. and 80° C. homogeneously, and subjecting to homogenization and emulsification for 3-8 minutes, adding the second gelling agent, then subjecting to homogenization for 7 to 15 minutes; and (4) shaping the mixture obtained in the step (3) to obtain the desired gel composition. Preferably, the shaping comprises one of the following methods:

(a) pouring the mixture obtained in the step (3) to a blister;

(b) filling the mixture obtained in the step (3) into a capsule; and/or (c) packaging the mixture obtained in the step (3) in a packaging material, preferably wherein the packaging material comprises one or more of an aluminum-plastic composite pouch and a packaging container made of a thermoresistant material.

In yet another embodiment of the present application, the use of the gel composition as described above in a food, medicine or health care product is also provided.

In another aspect, the present invention also provides an edible composition, which comprises the above-mentioned gel composition.

In one embodiment, the edible composition is a food, medicine or health care product.

DETAILED DESCRIPTION OF THE INVENTION

Figure 1:
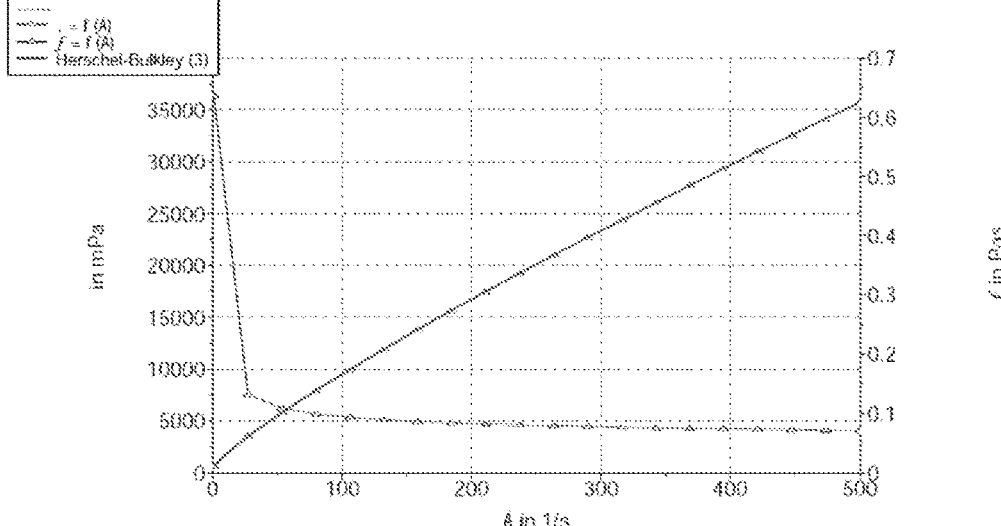
FIG. 1 shows a test sample of a fish oil (no hydrogenated palm oil) with a viscosity coefficient of 0.85.

For the purpose of the detailed description below, it is to be understood that various alternative changes to a component and sequences of steps may be adopted in this application, unless indicated to the contrary. In addition, unless in any working examples, or where otherwise indicated, all numbers representing quantities of ingredients used in, for example, the specification and claims should be understood as being modified by the term "about" in all cases. Therefore, unless indicated to the contrary, the numerical parameters set forth in the following specification and claims are approximate values that vary according to the desired performance to be obtained in this application and at least is not intended to limit the application of the principle of equivalence to the scope of the claims. Each numerical parameter should at least be interpreted based on the number of significant figures reported and through the application of ordinary rounding techniques.

Although the numerical ranges and parameters set forth in the broad range of this application are approximate values, the numerical values listed in the specific examples are reported as accurately as possible. However, any numerical value inherently contains certain errors that inevitably result from the standard deviation found in its respective test measurement.

In addition, it is to be understood that any numerical range described herein is intended to include all sub-ranges subsumed therein. For example, the range of "1 to 10" is intended to include all sub-ranges between (and including) the minimum value of 1 and the maximum value of 10, that is, having a minimum value equal to or greater than 1 and a maximum value equal to or less than 10.

In this application, unless expressly stated otherwise, the use of the singular includes the plural and the plural includes the singular. In addition, in this application, unless expressly stated otherwise, the use of "or" means "and/or", even if "and/or" can be used explicitly in some cases. In addition, in this application, unless expressly stated otherwise, the use of "a" or "an" means "at least one." For example, "a" polymer, "a" composition, etc. refer to any one or more of these items.

In one embodiment of the present application, a chewable and edible oil-in-water gel composition is provided. In another embodiment of the present application, a stable chewable gel composition with a high oil content is provided.

As used herein, the term "oil" has the conventional meaning in the pharmaceutical, food, and health care product industries, namely, fatty acid triglycerides. The oils that can be used in the gel composition of the present application can be various oils commonly used in the fields of medicine, food and health care products, such as vegetable oil or animal oil or a mixture thereof. In one aspect, the oil used in the gel composition of the present application is an oil rich in an unsaturated fatty acid or its esters, and more preferably, a fish oil and/or an algae oil. In a further aspect, the oil may also contain one or more biologically active ingredients that can be used in foods, medicines and/or health care products. As used herein, the term "biologically active ingredient" refers to an ingredient capable of exerting a certain effect on an organism. The biologically active ingredient that can be used in the gel composition of the present application include, but are not limited to an oil-soluble vitamin and the like.

As used herein, the term "high oil content" refers to a product having an oil content of 50 wt % or more. For example, the high oil content can refer to a product having 55 wt % or more, 60 wt % or more, 65 wt % or more up to 70 wt % or less, 75 wt % or less, 80 wt % or less, 85 wt % or less, 90 wt % or less, 95 wt % or less, or even 100 wt % or less of oil content. In the embodiment of the present application, preferably, the gel composition has an oil content of 50 wt % to 80 wt %. More preferably, the gel composition has an oil content of 55 wt % to 70 wt %. The above weight percentages are based on the total weight of the gel composition. In one embodiment of the present application, the oil-in-water gel composition contains an oil other than hydrogenated palm oil and/or palm stearin. Preferably, the oil content ranges from 55 to 70 wt %.

As used herein, the term "stable" means that a product will not undergo oil-water separation during a relatively long storage time (for example, 1 year or more, preferably 2 years or more). The "stable" gel composition as described in this application will not exhibit oil-water separation within the specified shelf life or more of a medicine, food or health care product, for example, and there will be notoil precipitation on the surface. Greasy taste may not be felt when such a gel composition is taken, and therefore the product flavor is improved. In addition, such a gel composition can also have an improved texture (such as hardness, elasticity, and cohesiveness, etc.) over a long period of time, thereby providing a better mouthfeel.

As used herein, the term "chewable" has its conventional meaning in the pharmaceutical, food, and health care product industries. In the embodiment of the present application, the gel composition exists in a form that can be broken or disrupted by chewing. The chewable gel composition as described in this application can be used in a nutritional supplement, for example, as or used in a medicine, food or health care product. Preferably, the gel composition described in the present application is the so-called "fish oil jelly" or "jelly fish oil".

As used herein, the term "gel" refers to a special semi-solid state transformed from a solution or sol under a certain condition (such as by the use of a gelling agent), in which a network structure filled with liquid as a dispersion medium in the structural voids is formed spatially by the use of a gelling agent. As used herein, the term "gelling agent" refers to an agent capable of gelling a solution or sol. In the embodiment of the present application, the gel composition is an "oil-in-water" type gel emulsion formed by using a specially selected gelling agent, in which the aqueous phase is gelled as the continuous phase and the oil phase as the discontinuous phase dispersed in the structural voids of the continuous phase. Suitable gelling agents are well known in the food, pharmaceutical and nutraceutical industries and are capable of solution/sol-gel conversion, including but not limited to gelatin, xanthan gum, carrageenan, pectin, konjac, acacia gum, locust bean gum, agar, gellan gum or a mixture of gelling agents, etc.

In one aspect of the present application, a chewable and edible oil-in-water gel composition is provided, which comprises a first gelling agent. In one embodiment, the chewable and edible oil-in-water gel composition further comprises a second gelling agent selected from xanthan gum, agar, gellan gum, locust bean gum, arabic gum, and modified starch.

In one aspect of the present application, a gel composition is provided, which includes a gelling agent, and the gelling agent may be a combination of the first gelling agent and the second gelling agent.

In various aspects of the present invention, the first gelling agent may be selected from gelatin, carrageenan, pectin, konjac gum, guar gum, and other gelling agents and mixtures thereof. Preferably, the first gelling agent may be gelatin, for example, gelatin that can be prepared from collagen of any mammal or collagen of any aquatic species. Preferably, the first gelling agent is gelatin and pectin, carrageenan and konjac gum, or carrageenan. Preferably, the mass ratio of gelatin to pectin ranges from 2:1 to 12:1. Preferably, the mass ratio of konjac gum to carrageenan ranges from 1:4 to 3:1. Based on the total weight of the gel composition, the first gelling agent may be 1 to 15 wt %, preferably 2 to 12 wt %. The second gelling agent may be selected from xanthan gum, agar, gellan gum, locust bean gum, arabic gum, modified starch and other gelling agents, and mixtures thereof. Preferably, the second gelling agent may be xanthan gum, arabic gum, arabic gum and modified starch, locust bean gum, or gellan gum. Preferably, the mass ratio of arabic gum to modified starch ranges from 3:1 to 5:1. Based on the total weight of the gel composition, the second gelling agent may be 0.1 to 2 wt %, preferably 0.2 to 1.0 wt %. Preferably, the gelling agent used in the gel composition of the present application is a combination of gelatin and xanthan gum, a combination of gelatin, gum acacia and modified starch, a combination of gelatin, pectin and gum acacia, a combination of carrageenan, konjac gum and locust bean gum, and the combination of carrageenan and gellan gum. Such a combination of gelling agents has the effects of significantly improving the water holding capacity of the composition and stabilizing the oil-water interface, thereby improving oil-water separation.

Figure 2:
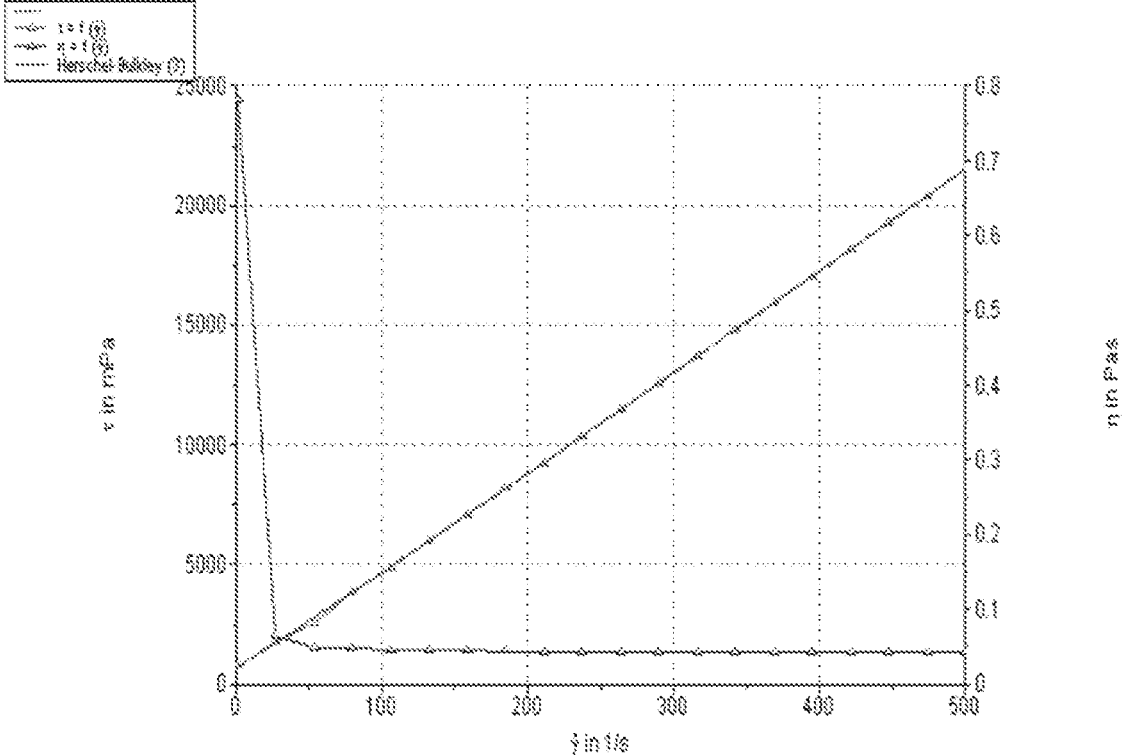
FIG. 2 shows a test sample of fish oil+hydrogenated palm oil with a viscosity coefficient of 1.03.

As used herein, the term "stabilizer" refers to an additive that has been found experimentally to be used in a formulation to improve the stability of the composition (such as light stability, thermal stability, storage stability), etc. For example, it has been found experimentally that hydrogenated palm oil has the effect of curing oils, and its effect can be tested by viscosity testing with a rotary rheometer. The results show that hydrogenated palm oil may increase the viscosity of the oil, thereby improving the stability of the oil in the system. The viscosity coefficient of a fish oil (without adding hydrogenated oil) is determined to be 0.85, and the viscosity coefficient of a fish oil plus hydrogenated palm oil is 1.03 (the test spectrum is shown in FIGS. 1 and 2). Specifically, the Hack Rotational Rheometer is used for viscosity measurement, in which the temperature is set to 25° C. and CR mode (controlling shear rate) is used. The test sample is placed on the test platform. The viscosity is measured according to the set parameters. The test sample is sheared by rotating using a test probe. The value is determined by a force-sensing element and transmitted to a software to display a shear stress corresponding to the shear rate in a quantified form. The sample used in FIG. 1 is a pure fish oil, and the sample used in FIG. 2 is a homogeneous mixture of a fish oil+5% hydrogenated palm oil heated and dissolved at a temperature between 60° C. and 80° C. and cooled. Viscosity is measured by the above method. The X axis represents the shear rate, the Y1 axis represents the shear stress, and the Y2 axis represents the viscosity. The viscosity coefficients of the two samples are obtained by fitting a curve. The larger the value, the higher the corresponding viscosity.

In the embodiment of the present application, the stabilizer that can be used in the gel composition of the present application can be selected from palm oil (which is formed by a processing method selected from a group consisting of hydrogenation, refining, transesterification, and fractionation and is a palm oil product having a melting point of 39 to 65° C.), phospholipid, phytosterol, edible waxes and other substances with similar effects and any combination thereof. Preferably, the stabilizer is selected from hydrogenated palm oil, palm stearin, phospholipid, beeswax and mixtures thereof. More preferably, the stabilizer is a mixture of hydrogenated palm oil, palm stearin, or beeswax and phospholipid. For example, the stabilizer may be a mixture of hydrogenated palm oil and phospholipid. In one aspect, the stabilizer may be a mixture of hydrogenated palm oil, palm stearin, or beeswax and phospholipid in a mass ratio of 3 to 15:1. Preferably, the stabilizer used in the present application is a mixture of (hydrogenated palm oil or palm stearin or beeswax):phospholipid in a mass ratio of (5 to 10):1. For example, without limitation, the phospholipid is in the range of 0.2 to 1 wt % based on the total weight of the gel composition. Alternatively, based on the total weight of the gel composition, hydrogenated palm oil, palm stearin or beeswax is in the range of 2 to 5 wt %, for example, 2 wt %, 2.5 wt %, 3 wt %, 3.5 wt %, 4 wt %, 4.5 wt %. The effect of solidifying the oil may be achieved by such a stabilizer which may have a significant role in the stability of the oil, thereby improving the stability of the gel composition. In addition, the use of phospholipid in the gel composition can also improve the fluidity of the composition.

In one embodiment, the oil-in-water gel composition contains 0.1 to 7 wt % of a stabilizer. In one embodiment, the stabilizer is a mixture of 2 to 5 wt % of hydrogenated palm oil, palm stearin or beeswax and 0.2 to 1 wt % of phospholipid.

The gel composition of the present application may optionally contain other additives that can be used in a medicine, food and/or health care product, including but not limited to a sweetener, an acid regulator, a filler, a flavoring agent, a coloring agent, and an antioxidants, etc.

In one aspect, the sweetener may be selected from xylitol, sorbitol, and other alditols. Preferably, the sweetener may make up 10 to 30 wt % of the total weight of the gel composition.

In another aspect, the acid regulator may be one or more of citric acid and its salts, malic acid, and other acid regulators. Preferably, the acid regulator may make up 0.05-0.5 wt % of the total weight of the gel composition.

In yet another aspect, the filler may be selected from resistant dextrin, inulin, and other fillers. Preferably, the filler may make up 0 to 5% of the total weight of the gel composition.

In yet another aspect, the flavoring agent may be a flavor, for example selected from an oil-soluble essence, a water-soluble essence, and other food essences. Preferably, the flavoring agent may make up 0 to 5 wt % of the total weight of the gel composition.

In still another aspect, the colorant may be a food-grade pigment or a colored fruit and vegetable juice, for example, selected from a food-grade pigment such as oil-soluble pigments and water-soluble pigments. Preferably, the colorant may make up 0 to 0.5 wt % of the total weight of the gel composition.

In yet another aspect, the antioxidant may be selected from vitamin E, rosemary extract, polyphenol, and other antioxidants. Preferably, the antioxidant may make up 0 to 0.5 wt % of the total weight of the gel composition.

In the embodiment of the present application, the gel composition further includes water to make up the gel composition to 100 wt %, that is, the balance is water. In one aspect, for example without limitation, water makes up 10 to 30 wt % of the total weight of the gel composition.

In another embodiment of the present application, a method for preparing the above-mentioned chewable and edible oil-in-water gel composition is also provided. The gel composition can be prepared by a method in which the first gelling agent, stabilizer and oil are mixed homogeneously and the resulting mixture is shaped.

In one aspect, the preparation method includes:

(1) heating the first gelling agent in water at a temperature between 60 and 80° C. until the first gelling agent completely dissolves;

(2) adding the stabilizer to the oil and mixing them homogeneously;

(3) mixing the mixture obtained in the step (1) and the mixture obtained in the step (2) at a temperature between 60° C. and 80° C. homogeneously, and subjecting to homogenization and emulsification for 3 to 8 minutes; and (4) shaping the mixture obtained in the step (3) to obtain the desired gel composition, wherein the shaping is one of the following methods:

(a) pouring the mixture obtained in the step (3) to a blister;

(b) filling the mixture obtained in the step (3) into a capsule; and (c) packaging the mixture obtained in the step (3) in a packaging material, wherein the packaging material comprises one or more of an aluminum-plastic composite pouch and a packaging container made of a thermoresistant material.

The preparation method may further include the following operations after homogeneous emulsification in step (3): adding a second gelling agent; then subjecting to homogenization and emulsification for 7 to 15 minutes; wherein the second gelling agent is selected from xanthan gum, agar, gellan gum, locust bean gum, arabic gum, and modified starch.

In another embodiment of the present application, a method for preparing the gel composition as described above is also provided. The gel composition can be prepared by a method in which the first gelling agent, stabilizer and oil are mixed homogeneously, the second gelling agent is then added and mixed homogeneously and the resulting mixture is shaped.

In one aspect, the preparation method includes:

(1) heating the first gelling agent in a suitable amount of water to completely dissolve the first gelling agent which is kept warm for use;

(2) adding the stabilizer to the oil and mixing them homogeneously which are kept warm for use;

(3) mixing the mixtures obtained in the step (1) and the step (2) at a temperature between 60° C. and 80° C. homogeneously, and subjecting to homogenization and emulsification with a homogenizer for about 5 to 10 minutes; adding the second gelling agent and subjecting to homogenization and emulsification for about 10 to 15 minutes; and (4) shaping the mixture obtained in the step (3) to obtain the desired gel composition.

In a further aspect, the preparation method includes:

(1) heating the first gelling agent and optionally a sweetener, an acid regulator, a colorant, a water-soluble flavoring agent in a suitable amount of water at a temperature between 60 and 80° C. until the first gelling agent completely dissolves and keeping the mixture warm for use;

(2) adding the stabilizer and optionally an antioxidant and an oil-soluble flavoring agent to the oil and mixing them homogeneously which are kept warm for use;

(3) adding the mixture obtained in the step (2) to the mixture obtained in the step (1) and mixing them at a temperature between 60° C. and 80° C. homogeneously, and subjecting to homogenization and emulsification with a homogenizer for 5 to 10 minutes; adding the second gelling agent and subjecting to homogenization for 10 to 15 minutes;

(4) shaping the mixture obtained in the step (3) to obtain the desired gel composition, wherein the shaping in the step (4) may comprise one of the following methods:

(a) pouring the mixture obtained in the step (3) to a blister;

(b) filling the mixture obtained in the step (3) into a capsule; and/or (c) packaging the mixture obtained in the step (3) in a packaging material.

Preferably, the packaging material comprises one or more of an aluminum-plastic composite pouch and a packaging container made of a thermoresistant material.

In another embodiment of the present application, the use of the gel composition as described above in a food, medicine or health care product is also provided. The food, medicine or health care product may be in a chewable form.

The application will be further explained in detail below with reference to the examples. However, those skilled in the art should understand that these examples are provided for illustrative purposes only, and are not intended to limit the application.

EXAMPLES

The embodiments of the present application will be described in detail below in conjunction with examples, but those skilled in the art will understand that the following examples are only used to illustrate the present application, and should not be regarded as limiting the scope of the present application. If specific conditions are not indicated in the examples, it shall be carried out in accordance with the conventional conditions or the conditions recommended by the manufacturer. When the manufacturer is not indicated in the examples, the reagents or instruments used are all conventional products that can be purchased commercially. Unless otherwise indicated, all amounts listed are described in parts by weight based on the total weight. This application should not be interpreted as being limited to the working examples described.

Preparation Method:

1. Aqueous phase: heating xylitol, sorbitol, potassium citrate, resistant dextrin, and the first gelling agent (e.g., gelatin, carrageenan) with an appropriate amount of water at 60° C. until the first gelling agent completely dissolves;

2. Oil phase: adding mixed tocopherol, lemon essence, hydrogenated palm oil, and phospholipid to an oil (for example, fish oil), mixing themhomogeneously and keeping them warm at 60° C. for use;

3. Adding the oil phase to the aqueous phase, stirring them homogeneously, homogenizing them at 60° C. in a homogenizer for 10 minutes, and pouring the resulting composition onto a blister for shaping; or after homogenization, further adding a second gelling agent (for example, xanthan gum, arabic gum), homogenizing for 10 minutes, and pouring the resulting composition onto a blister for shaping.

According to the above preparation method, the gel compositions 1 to 25 were prepared, and the specific components are listed in Table 1 below.

Test Method:

Texture Test:

The texture test was performed on the prepared gel composition using a texture analyzer according to the TPA method. 20 parallel samples of each gel composition were taken, and the average of the measured values was taken as the measurement result. The results are reported in Table 1 below.

The texture test was performed as described below.

1. A texture analyzer was used to perform the texture test by the TPA method (texture profile analysis), which is a general method for testing texture characteristics in the industry, also known as the secondary chewing test, using the test probe to secondary compress samples. The index was quantified by a force sensing element.

2. Testing process: The sample was placed in the middle of the test bench. The TPA method was selected and the test button was started to perform the test. The parallel test was repeated with 20 samples.

3. Data processing: The test results of each sample were recorded by the force sensing element of the instrument and then processed by software and finally presented as specific values. The average value of indicators for 20 parallel samples was taken as the result output, which was scored and evaluated.

Oil Precipitation Test:

A centrifuge was used to test the degree of oil precipitation of the obtained gel composition. The emulsion of the same amount was taken and centrifuged at a high speed for layering. The precipitated oil layer was separated and weighed. 3 parallel samples of each gel composition were taken and the average of the measured values was used as the measurement result. The results were reported in Table 1 below.

The oil precipitation test was carried out as follows:

1. Test conditions. The instrument was a centrifuge which was hold at a temperature of 55° C. The speed was set to 8000 rpm, and the centrifugation time was 5 min;

2. Measurement process. A certain amount of emulsion before shaping was weighted and into a centrifuge tube, and the total weight of the emulsion and the centrifuge tube was recorded. Then, the same amount of water was added to the centrifuge tube which was placed symmetrically in the centrifuge. The centrifugation was performed under the above test condition. After centrifugation, the upper layer of oil was taken using a pipette and then the centrifuge tube and the remaining emulsion were weighted. The weight was determined in triplicate.

3. Data processing: The amount of oil precipitation was the difference between the total weight before centrifugation and the total weight after centrifugation. The amount of oil precipitation was converted to a value in g/10 g of the gel composition. The data of 3 parallel samples were used as the result outputs which were used to perform scoring test.

The test data of the texture test and the oil precipitation test of the tested gel composition were scored and were all represented as a score. Finally, the scores were summed to comprehensively evaluate the effects of each composition in the Examples with the total score.

Hardness (g): <6500 was counted as 1 point; 6500 to 6999 as 2 points; 7000 to 7499 as 3 points; 7500 to 7999 as 4 points; 8000 to 8499 as 5 points; 8500 to 8999 as 4 Points; 9000 to 9499 as 3 points; 9500 to 9999 as 2 points; and ≥10000 as 1 point.

Elasticity: <0.60 was counted as 1 point; 0.60 to 0.69 as 2 points; 0.70 to 0.79 as 3 points; 0.80 to 0.89 as 4 points; 0.90 to 0.99 as 5 points; 1.00 to 1.09 as 4 points; 1.10 to 1.19 as 3 points; 1.20 to 1.29 as 2 points; and 1.30 to 1.39 as 1 point.

Cohesiveness: <0.50 was counted as 1 point; 0.50 to 0.59 as 2 points; 0.60 to 0.69 as 3 points; 0.70 to 0.79 as 4 points; 0.80 to 0.89 as 5 points; 0.90 to 0.99 as 4 points; 1.00 to 1.09 as 3 points; 1.10 to 1.19 as 2 points; 1.20 to 1.29 as 1 point.

Oil precipitation (g/10 g): ≥0.90 was counted as 1 point; 0.80 to 0.89 as 2 points; 0.70 to 0.79 as 3 points; 0.6 to 0.69 as 4 points; <0.6 as 5 points.

TABLE 1

The contents of the components and test results of the gel compositions and the comparative composition according to the application

| Composition No. | 1 | 2 | 3 | 4 | 5 | 6 | 7 |
|---|---|---|---|---|---|---|---|
| gelatin | 4 | 4 | 4 | 4 | 4 | 4 | 4 |
| xylitol | 8 | 8 | 8 | 8 | 8 | 8 | 8 |
| sorbitol | 2 | 2 | 2 | 2 | 2 | 2 | 2 |
| fish oil | 55 | 55 | 55 | 55 | 55 | 55 | 55 |
| vitamin E | 0.3 | 0.3 | 0.3 | 0.3 | 0.3 | 0.3 | 0.3 |
| citric acid monohydrate | 0.05 | 0.05 | 0.05 | 0.05 | 0.05 | 0.05 | 0.05 |
| lemon essence | 0.2 | 0.2 | 0.2 | 0.2 | 0.2 | 0.2 | 0.2 |
| resistant dextrin | 0.5 | 0.5 | 0.5 | 0.5 | 0.5 | 0.5 | 0.5 |
| water | 29.75 | 28.95 | 29.95 | 27.95 | 23.95 | 26.15 | 29.75 |
| xanthan gum | 0.2 | 1.0 | 0 | 0 | 0 | 0.4 | 0 |
| hydrogenated palm oil | 0 | 0 | 0 | 2 | 6 | 3 | 0 |
| phospholipid | 0 | 0 | 0 | 0 | 0 | 0.4 | 0.2 |

13 14

TABLE 1-continued

The contents of the components and test results of the gel compositions
and the comparative composition according to the application

| | | | | | | | |
|---|---|---|---|---|---|---|---|
| beeswax | 0 | 0 | 0 | 0 | 0 | 0 | 0 |
| palm stearin | 0 | 0 | 0 | 0 | 0 | 0 | 0 |
| Glyceryl Monostearate | 0 | 0 | 0 | 0 | 0 | 0 | 0 |
| Hardness | 3 | 3 | 3 | 3 | 3 | 5 | 3 |
| Elasticity | 4 | 3 | 2 | 3 | 3 | 5 | 3 |
| Cohesiveness | 3 | 4 | 2 | 3 | 3 | 5 | 2 |
| Oil precipitation | 2 | 2 | 1 | 3 | 4 | 5 | 3 |
| composite score | 12 | 12 | 8 | 12 | 13 | 20 | 11 |

| Composition No. | 8 | 9 | 10 | 11 | 12 | 13 | 14 |
|---|---|---|---|---|---|---|---|
| gelatin | 4 | 4 | 4 | 4 | 4 | 4 | 4 |
| xylitol | 8 | 8 | 8 | 8 | 8 | 8 | 8 |
| sorbitol | 2 | 2 | 2 | 2 | 2 | 2 | 2 |
| fish oil | 55 | 55 | 55 | 55 | 60 | 70 | 55 |
| vitamin E | 0.3 | 0.3 | 0.3 | 0.3 | 0.3 | 0.3 | 0.3 |
| citric acid monohydrate | 0.05 | 0.05 | 0.05 | 0.05 | 0.05 | 0.05 | 0.05 |
| lemon essence | 0.2 | 0.2 | 0.2 | 0.2 | 0.2 | 0.2 | 0.2 |
| resistant dextrin | 0.5 | 0.5 | 0.5 | 0.5 | 0.5 | 0.5 | 0.5 |
| water | 28.95 | 26.55 | 29.15 | 26.55 | 21.15 | 11.15 | 27.55 |
| xanthan gum | 0 | 0 | 0.4 | 0.4 | 0.4 | 0.4 | 0 |
| hydrogenated palm oil | 0 | 3 | 0 | 3 | 3 | 3 | 2 |
| beeswax | 0 | 0 | 0 | 0 | 0 | 0 | 0 |
| palm stearin | 0 | 0 | 0 | 0 | 0 | 0 | 0 |
| phospholipid | 1.0 | 0.4 | 0.4 | 0 | 0.4 | 0.4 | 0.4 |
| Glyceryl Monostearate | 0 | 0 | 0 | 0 | 0 | 0 | 0 |
| Hardness | 3 | 4 | 4 | 4 | 5 | 5 | 4 |
| Elasticity | 2 | 4 | 4 | 3 | 5 | 5 | 4 |
| Cohesiveness | 3 | 4 | 4 | 4 | 5 | 5 | 3 |
| Oil precipitation | 3 | 4 | 3 | 4 | 4 | 4 | 4 |
| composite score | 11 | 16 | 15 | 15 | 19 | 19 | 15 |

| Composition No. | 15 | 16 | 17 | 18 | 19 | 20 | 21 |
|---|---|---|---|---|---|---|---|
| gelatin | 4 | 4 | 4 | 4 | 4 | 4 | 4 |
| xylitol | 8 | 8 | 8 | 8 | 8 | 8 | 8 |
| sorbitol | 2 | 2 | 2 | 2 | 2 | 2 | 2 |
| fish oil | 55 | 55 | 55 | 55 | 55 | 55 | 55 |
| vitamin E | 0.3 | 0.3 | 0.3 | 0.3 | 0.3 | 0.3 | 0.3 |
| citric acid monohydrate | 0.05 | 0.05 | 0.05 | 0.05 | 0.05 | 0.05 | 0.05 |
| lemon essence | 0.2 | 0.2 | 0.2 | 0.2 | 0.2 | 0.2 | 0.2 |
| resistant dextrin | 0.5 | 0.5 | 0.5 | 0.5 | 0.5 | 0.5 | 0.5 |
| water | 25.65 | 27.25 | 29.55 | 26.95 | 29.55 | 27.75 | 27.95 |
| xanthan gum | 0 | 0 | 0.4 | 0 | 0 | 0 | 0 |
| hydrogenated palm oil | 4 | 2 | 0 | 3 | 0 | 2 | 0 |
| phospholipid | 0.3 | 0.7 | 0 | 0 | 0.4 | 0.2 | 0 |
| beeswax | 0 | 0 | 0 | 0 | 0 | 0 | 0 |
| palm stearin | 0 | 0 | 0 | 0 | 0 | 0 | 0 |
| Glyceryl Monostearate | 0 | 0 | 0 | 0 | 0 | 0 | 2 |
| Hardness | 3 | 3 | 3 | 3 | 3 | 4 | 2 |
| Elasticity | 4 | 3 | 4 | 3 | 3 | 3 | 2 |
| Cohesiveness | 2 | 2 | 3 | 3 | 3 | 4 | 2 |
| Oil precipitation | 4 | 4 | 3 | 4 | 3 | 4 | 1 |
| composite score | 13 | 13 | 13 | 13 | 12 | 15 | 7 |

| Composition No. | 22 | 23 | 24 | 25 | 26 | 27 | 28 |
|---|---|---|---|---|---|---|---|
| gelatin | 4 | 4 | 4 | 4 | 4 | 4 | 4 |
| xylitol | 8 | 8 | 8 | 8 | 8 | 8 | 8 |
| sorbitol | 2 | 2 | 2 | 2 | 2 | 2 | 2 |
| fish oil | 55 | 55 | 55 | 55 | 55 | 60 | 70 |
| vitamin E | 0.3 | 0.3 | 0.3 | 0.3 | 0.3 | 0.3 | 0.3 |
| citric acid monohydrate | 0.05 | 0.05 | 0.05 | 0.05 | 0.05 | 0.05 | 0.05 |
| lemon essence | 0.2 | 0.2 | 0.2 | 0.2 | 0.2 | 0.2 | 0.2 |
| resistant dextrin | 0.5 | 0.5 | 0.5 | 0.5 | 0.5 | 0.5 | 0.5 |
| water | 24.55 | 26.15 | 22.35 | 24.75 | 25.15 | 20.15 | 10.15 |
| xanthan gum | 0.4 | 0.4 | 0.4 | 0.6 | 0.4 | 0.4 | 0.4 |
| hydrogenated palm oil | 3 | 0 | 6 | 4 | 0 | 0 | 0 |
| phospholipid | 2 | 0.4 | 1.2 | 0.6 | 0.4 | 0.4 | 0.4 |
| beeswax | 0 | 0 | 0 | 0 | 4 | 4 | 4 |
| palm stearin | 0 | 0 | 0 | 0 | 0 | 0 | 0 |
| Glyceryl Monostearate | 0 | 3 | 0 | 0 | 0 | 0 | 0 |
| Hardness | 2 | 4 | 2 | 4 | 4 | 4 | 4 |

TABLE 1-continued

The contents of the components and test results of the gel compositions
and the comparative composition according to the application

| Elasticity | 3 | 4 | 2 | 5 | 5 | 5 | 5 |
|---|---|---|---|---|---|---|---|
| Cohesiveness | 2 | 4 | 3 | 5 | 4 | 4 | 4 |
| Oil precipitation | 2 | 3 | 2 | 5 | 5 | 4 | 4 |
| composite score | 9 | 15 | 9 | 19 | 18 | 17 | 17 |

| Composition No. | 29 | 30 | 31 |
|---|---|---|---|
| gelatin | 4 | 4 | 4 |
| xylitol | 8 | 8 | 8 |
| sorbitol | 2 | 2 | 2 |
| fish oil | 55 | 60 | 70 |
| vitamin E | 0.3 | 0.3 | 0.3 |
| citric acid monohydrate | 0.05 | 0.05 | 0.05 |
| lemon essence | 0.2 | 0.2 | 0.2 |
| resistant dextrin | 0.5 | 0.5 | 0.5 |
| water | 26.15 | 21.15 | 11.15 |
| xanthan gum | 0.4 | 0.4 | 0.4 |
| hydrogenated palm oil | 0 | 0 | 0 |
| phospholipid | 0.4 | 0.4 | 0.4 |
| beeswax | 0 | 0 | 0 |
| palm stearin | 3 | 3 | 3 |
| Glyceryl Monostearate | 0 | 0 | 0 |
| Hardness | 5 | 5 | 4 |
| Elasticity | 5 | 5 | 5 |
| Cohesiveness | 4 | 4 | 4 |
| Oil precipitation | 4 | 4 | 4 |
| composite score | 18 | 18 | 17 |

| Composition No. | 32 | 33 | 34 | 35 | 36 | 37 | 38 |
|---|---|---|---|---|---|---|---|
| gelatin | 1 | 15 | 8 | 2 | 2 | 6 | 0 |
| carrageenin | 0 | 0 | 0 | 0 | 0 | 0 | 0.5 |
| acacia gum | 0 | 0 | 0.5 | 1.5 | 2 | 0.5 | 0 |
| modified starch | 0 | 0 | 0.1 | 0.5 | 0 | 0 | 0 |
| gellan gum | 0 | 0 | 0 | 0 | 0 | 0 | 0 |
| locust bean gum | 0 | 0 | 0 | 0 | 0 | 0 | 2 |
| pectin | 0 | 0 | 0 | 0 | 1 | 0.5 | 0 |
| konjak gum | 0 | 0 | 0 | 0 | 0 | 0 | 1.5 |
| xylitol | 8 | 8 | 8 | 8 | 8 | 8 | 8 |
| sorbitol | 2 | 2 | 2 | 2 | 2 | 2 | 2 |
| fish oil | 60 | 60 | 60 | 60 | 60 | 60 | 60 |
| vitamin E | 0.3 | 0.3 | 0.3 | 0.3 | 0.3 | 0.3 | 0.3 |
| citric acid monohydrate | 0.05 | 0.05 | 0.05 | 0.05 | 0.05 | 0.05 | 0.05 |
| lemon essence | 0.2 | 0.2 | 0.2 | 0.2 | 0.2 | 0.2 | 0.2 |
| resistant dextrin | 0.5 | 0.5 | 0.5 | 0.5 | 0.5 | 0.5 | 0.5 |
| water | 18.95 | 12.65 | 16.95 | 21.55 | 20.55 | 18.55 | 21.55 |
| xanthan gum | 2 | 0.1 | 0 | 0 | 0 | 0 | 0 |
| hydrogenated palm oil | 6 | 1 | 3 | 3 | 3 | 3 | 3 |
| phospholipid | 1 | 0.2 | 0.4 | 0.4 | 0.4 | 0.4 | 0.4 |
| beeswax | 0 | 0 | 0 | 0 | 0 | 0 | 0 |
| palm stearin | 0 | 0 | 0 | 0 | 0 | 0 | 0 |
| Glyceryl Monostearate | 0 | 0 | 0 | 0 | 0 | 0 | 0 |
| Hardness | 4 | 5 | 5 | 4 | 4 | 5 | 4 |
| Elasticity | 5 | 4 | 4 | 5 | 4 | 4 | 4 |
| Cohesiveness | 4 | 5 | 4 | 4 | 4 | 4 | 4 |
| Oil precipitation | 5 | 4 | 4 | 4 | 5 | 4 | 4 |
| composite score | 18 | 18 | 17 | 17 | 17 | 17 | 16 |

| Composition No. | 39 | 40 | 41 |
|---|---|---|---|
| gelatin | 0 | 0 | 0 |
| carrageenin | 2 | 1.0 | 2.5 |
| acacia gum | 0 | 0 | 0 |
| modified starch | 0 | 0 | 0 |
| gellan gum | 0 | 2 | 0.2 |
| locust bean gum | 0.2 | 0 | 0 |
| pectin | 0 | 0 | 0 |
| konjak gum | 0.5 | 0 | 0 |
| xylitol | 8 | 8 | 8 |
| sorbitol | 2 | 2 | 2 |
| fish oil | 60 | 60 | 60 |
| vitamin E | 0.3 | 0.3 | 0.3 |
| citric acid monohydrate | 0.05 | 0.05 | 0.05 |
| lemon essence | 0.2 | 0.2 | 0.2 |
| resistant dextrin | 0.5 | 0.5 | 0.5 |
| water | 22.85 | 23.05 | 22.85 |
| xanthan gum | 0 | 0 | 0 |

TABLE 1-continued

| The contents of the components and test results of the gel compositions and the comparative composition according to the application | | | |
| --- | --- | --- | --- |
| hydrogenated palm oil | 3 | 3 | 3 |
| phospholipid | 0.4 | 0.4 | 0.4 |
| beeswax | 0 | 0 | 0 |
| palm stearin | 0 | 0 | 0 |
| Glyceryl Monostearate | 0 | 0 | 0 |
| Hardness | 5 | 4 | 5 |
| Elasticity | 3 | 5 | 3 |
| Cohesiveness | 4 | 3 | 4 |
| Oil precipitation | 4 | 4 | 4 |
| composite score | 16 | 16 | 16 |

As can be seen from the above table, the gel compositions of the present application (including the combination of the first gelling agent (gelatin) and the second gelling agent (xanthan gum) and the stabilizers (hydrogenated palm oil or palm stearin or beeswax+phospholipid)) have a superior performance (5 points) in terms of the most indicators of the textures (hardness, elasticity and cohesiveness) and oil precipitation, and achieve 4 points in terms of only a few indicators, showing an excellent comprehensive performance (a comprehensive score is close to or equal to full marks, 20 points). In addition, the oil content contained in the gel composition according to the present application can be up to 70 wt % of the total weight of the compositions.

When only the first gelling agent (gelatin) and the second gelling agent (xanthan gum) are used without the stabilizers and when the compositions have the same oil content of 55 wt %, the resulting gel compositions can only reach low scores or moderate scores (between 1 and 3 points) in terms of the most indicators of the textures (hardness, elasticity and cohesiveness) and oil precipitation, and only can achieve 4 points in terms of a few indicators. The comprehensive scores are ordinary or even not good (between 8 and 12 points).

When only the first gelling agent (gelatin) and a stabilizer (hydrogenated palm oil or palm stearin or beeswax) are used without the second gelling agent (xanthan gum) and a component of the stabilizers (phospholipid) and when the compositions have the same oil content of 55 wt %, the resulting gel compositions can only achieve moderate scores (between 3 and 4 points) in terms of the texture (hardness, elasticity and cohesiveness) and oil precipitation. The comprehensive scores are ordinary (between 12 and 13 points).

When only the first gelling agent (gelatin) and a component of the stabilizers (phospholipid) are used without the second gelling agent (xanthan gum) and another component of the stabilizers (hydrogenated palm oil or palm stearin or beeswax) and when the compositions have the same oil content of 55 wt %, the resulting gel compositions can only achieve low or moderate scores (between 2 and 3 points) in terms of the texture (hardness, elasticity and cohesiveness) and oil precipitation. The comprehensive scores are average (between 11 and 12 points).

When only the first gelling agent (gelatin) and the stabilizer (hydrogenated palm oil or palm stearin or beeswax+phospholipid, and the mass ratio of hydrogenated palm oil:phospholipid ranges from 5:1 to 10:1) are used without the second gelling agent (xanthan gum) and when the compositions have the same oil content of 55 wt %, the resulting gel compositions achieve moderate scores (4 points) in terms of the most indicators of the texture (hardness, elasticity and cohesiveness) and oil precipitation and achieve 3 points in terms of a few indicators. The comprehensive score are above average (between 15 and 16 points), but still lower than those achieved by the gel compositions of the present application.

When only the first gelling agent (gelatin) is used without the second gelling agent (xanthan gum) and the stabilizer (hydrogenated palm oil or palm stearin or beeswax+phospholipid) and when the compositions have the same oil content of 55 wt %, the resulting gel compositions perform poorly in terms of the texture (hardness, elasticity and cohesiveness) and oil precipitation, or only reach moderate scores (between 1 and 3 points) in terms of a few indicators. The comprehensive scores are poor (only 8 points).

When a monoglyceride with similar properties is substituted for hydrogenated palm oil or palm stearin or beeswax as a component of the stabilizers and added to the gel composition together with the first gelling agent (gelatin), the second gelling agent (xanthan gum) and a component of the stabilizers (phospholipid) and when the compositions have the same oil content of 55 wt %, the resulting gel compositions perform poorly in terms of the texture (hardness, elasticity and cohesiveness) and oil precipitation, or only reach moderate scores (between 1 and 4 points). The comprehensive scores are low or moderate (7 points and 15 points).

When beeswax is substituted for hydrogenated palm oil as a component of the stabilizers and added to the gel composition together with the first gelling agent (gelatin), the second gelling agent (xanthan gum) and a component of the stabilizers (phospholipid) and when the compositions have the same oil content of 55 wt %, the resulting gel compositions can achieve excellent or moderate scores (between 4 and 5 points) in terms of the texture (hardness, elasticity and cohesiveness) and oil precipitation. The comprehensive scores are above average (between 17 and 18 points).

When palm stearin is substituted for hydrogenated palm oil as a component of the stabilizers and added to the gel composition together with the first gelling agent (gelatin), the second gelling agent (xanthan gum) and a component of the stabilizers (phospholipid) and when the compositions have the same oil content of 55 wt %, the resulting gel compositions can achieve excellent or moderate scores (between 4 and 5 points) in terms of the texture (hardness, elasticity and cohesiveness) and oil precipitation. The comprehensive scores are above average (between 17 and 18 points).

When the first gelling agent (gelatin), the second gelling agent (arabic gum and modified starch) and the stabilizers (hydrogenated palm oil or palm stearin or beeswax+phospholipid) are used and when the compositions have the same oil content of 60 wt %, the resulting gel compositions can achieve excellent or moderate scores (between 4 and 5 points) in terms of the texture (hardness, elasticity and cohesiveness) and oil precipitation. The comprehensive scores are above average (17 points).

When the first gelling agent (gelatin and pectin), the second gelling agent (arabic gum) and the stabilizers (hydrogenated palm oil or palm stearin or beeswax+phospholipid) are used and when the compositions have the same oil content of 60 wt %, the resulting gel compositions can achieve excellent or moderate scores (between 4 and 5 points) in terms of the texture (hardness, elasticity and cohesiveness) and oil precipitation. The comprehensive scores are above average (17 points).

When the first gelling agent (carrageenan and konjac gum), the second gelling agent (locust bean gum) and the stabilizers (hydrogenated palm oil or palm stearin or beeswax+phospholipid) are used and when the compositions have the same oil content of 60 wt %, the resulting gel compositions can achieve moderate scores (between 4 and 5 points) in terms of the most indicators of the texture (hardness, elasticity and cohesiveness) and oil precipitation and can achieve 5 and 3 points in terms of a few indicators. The comprehensive scores are above average (16 points).

When the first gelling agent (carrageenan), the second gelling agent (gellan gum) and the stabilizers (hydrogenated palm oil or palm stearin or beeswax+phospholipid) are used and the compositions have the same oil content of 60 wt %, the resulting gel compositions can achieve average scores or more (between 3 and 5 points) in terms of the texture (hardness, elasticity and cohesiveness) and oil precipitation. The comprehensive scores are above average (16 points).

It can be seen that this application has achieved the effects of improving oil stability and improving the texture of the compositions by using a specially selected combination of gelling agents and stabilizers. In particular, the stability of the composition is improved by addition of the specially selected stabilizers at a ratio. When the second gelling agent is added in a specific ratio, the water holding capacity of the composition is better, thereby improving oil-water separation and obtaining a composition with a better oil content.

The invention claimed is:

1. A gel composition, characterized in that, based on total weight of the gel composition, the gel composition comprises:
   (1) 1 to 15 wt % of a first gelling agent, wherein the first gelling agent is selected from a group consisting of gelatin, carrageenan, pectin, konjac gum, and guar gum;
   (2) 0.1 to 7 wt % of a stabilizer, wherein the stabilizer is a mixture of 2 to 5 wt % of a hydrogenated palm oil, a palm stearin or a beeswax and 0.2 to 1 wt % of a phospholipid; and
   (3) 55 to 70 wt % of an oil other than the hydrogenated palm oil and the palm stearin,
   wherein the stabilizer is a mixture of one of hydrogenated palm oil, palm stearin and beeswax with the phospholipid, and wherein a mass ratio of hydrogenated palm oil, palm stearin or beeswax and the phospholipid is 5 to 10:1.

2. The gel composition of claim 1, characterized in that the gel composition further comprises a second gelling agent selected from a group consisting of xanthan gum, agar, gellan gum, locust bean gum, arabic gum, and modified starch.

3. The gel composition of claim 2, characterized in that the first gelling agent is gelatin, and the second gelling agent is xanthan gum.

4. The gel composition of claim 1, characterized in that the melting point of the hydrogenated palm oil or palm stearin ranges from 39° C. to 65° C.

5. The gel composition of claim 1, characterized in that the oil is an unsaturated fatty acid or its ester.

6. The gel composition of claim 5, characterized in that the oil is an animal oil, a vegetable oil, or a combination thereof.

7. The gel composition of claim 1, characterized in that the gel composition further comprises an additive useful in a medicine, food, or health care product, wherein the additive is one or more of a sweetener, an acid regulator, a filler, a flavoring agent, a coloring agent, and an antioxidant.

8. The gel composition of claim 7, characterized in that the sweetener is xylitol, and/or sorbitol; the acid regulator is citric acid and its salts, and/or malic acid; the filler is resistant dextrin, and/or inulin; the flavoring agent is an oil-soluble essence, and/or a water-soluble essence; the coloring agent is an oil-soluble pigment and/or a water-soluble pigment; the antioxidant is vitamin E, rosemary extract, and/or polyphenols.

9. The gel composition of claim 1, characterized in that the aqueous phase of the gel composition further comprises a water-soluble active ingredient, wherein the active ingredient is selected from a group consisting of a water-soluble vitamin, a water-soluble dietary fiber and a mineral; and the oil phase of the gel composition further includes an oil soluble vitamin.

10. A method for preparing the gel composition of claim 1, comprising:
   (1) heating the first gelling agent in water at a temperature between 60° C. and 80° C. until the first gelling agent completely dissolves;
   (2) adding the stabilizer to the oil and mixing them homogeneously;
   (3) mixing homogeneously the mixture obtained in the step (1) and the mixture obtained in the step (2) at a temperature between 60° C. and 80° C., and subjecting to homogenization and emulsification for 3 to 8 minutes; and
   (4) shaping the mixture obtained in the step (3) to obtain the desired gel composition, wherein the shaping is achieved by one of the following methods:
      (a) pouring the mixture obtained in the step (3) to a blister;
      (b) filling the mixture obtained in the step (3) into a capsule; and
      (c) packaging the mixture obtained in the step (3) in a packaging material, wherein the packaging material comprises one or more of an aluminum-plastic composite pouch and a packaging container made of a thermoresistant material,
   wherein the stabilizer is a mixture of one of hydrogenated palm oil, palm stearin and beeswax with the phospholipid, where a mass ratio of hydrogenated palm oil, palm stearin or beeswax with the phospholipid is 5 to 10:1.

11. The method of claim 10, characterized in that, the method comprises the following steps after the homogenization and emulsification in the step (3): adding a second gelling agent; then subjecting to homogenization and emulsification for 7 to 15 minutes; wherein the second gelling agent is one or more of xanthan gum, agar, gellan gum, locust bean gum, acacia gum, and modified starch.

12. The gel composition of claim 1, wherein the gel composition is a chewable and edible oil-in-water gel composition.

13. The gel composition of claim 6, wherein the oil is a fish oil, an algae oil or a combination thereof.

\* \* \* \* \*